(12) United States Patent
Kawakami

(10) Patent No.: US 7,497,852 B2
(45) Date of Patent: Mar. 3, 2009

(54) PULL-ON DISPOSABLE WEARING ARTICLE

(75) Inventor: Yusuke Kawakami, Kagawa-ken (JP)

(73) Assignee: Uni-Charm Corporation, Ehime-ken (JP)

( * ) Notice: Subject to any disclaimer, the term of this patent is extended or adjusted under 35 U.S.C. 154(b) by 0 days.

(21) Appl. No.: 11/380,321

(22) Filed: Apr. 26, 2006

(65) Prior Publication Data

US 2006/0247595 A1 Nov. 2, 2006

(30) Foreign Application Priority Data

Apr. 27, 2005 (JP) ............................. 2005-129994

(51) Int. Cl.
*A61F 13/15* (2006.01)
(52) U.S. Cl. .................. 604/391; 604/387; 604/396
(58) Field of Classification Search ............ 604/385.01, 604/385.03, 386–387, 391, 395–396
See application file for complete search history.

(56) References Cited

U.S. PATENT DOCUMENTS

| | | | |
|---|---|---|---|
| 5,074,854 A | 12/1991 | Davis | |
| 5,370,634 A | 12/1994 | Ando et al. | |
| 5,531,732 A * | 7/1996 | Wood | ........................ 604/391 |
| 5,624,428 A * | 4/1997 | Sauer | ........................ 604/391 |
| 5,662,638 A | 9/1997 | Johnson et al. | |
| 6,210,388 B1 * | 4/2001 | Widlund et al. | ............. 604/390 |
| 6,287,287 B1 | 9/2001 | Elsberg | |
| 6,579,275 B1 * | 6/2003 | Pozniak et al. | .............. 604/390 |
| 6,972,012 B1 * | 12/2005 | Pozniak et al. | .............. 604/386 |
| 7,393,347 B2 * | 7/2008 | Otsubo et al. | .......... 604/385.01 |
| 2006/0089616 A1 | 4/2006 | Belau et al. | |
| 2006/0282057 A1 * | 12/2006 | Otsubo et al. | .......... 604/385.13 |

FOREIGN PATENT DOCUMENTS

| | | |
|---|---|---|
| JP | 5-317356 | 12/1993 |
| JP | 6-31725 | 4/1994 |
| JP | 2003-339772 A | 12/2003 |
| WO | 97/13485 * | 4/1997 |
| WO | 2004/047704 | 6/2004 |
| WO | 2006134895 A1 | 12/2006 |

* cited by examiner

*Primary Examiner*—Michele Kidwell
(74) *Attorney, Agent, or Firm*—Lowe Hauptman Ham & Berner, LLP

(57) ABSTRACT

A disposable diaper includes a front panel and a rear panel connected to each other, tear-apart zones provided at side edges of a waist region, in which the front and rear panels can be disconnected from each other, fastening members provided on the side of inner surface of the rear panel in a vicinity of the respective tear-apart zones and adapted to reconnect the disconnected front and rear panels to each other and cover members provided on the side of the inner surface of the rear panel so as to cover the tear-apart zones as well as the fastening members.

19 Claims, 6 Drawing Sheets

PULL-ON DISPOSABLE WEARING ARTICLE

BACKGROUND OF THE INVENTION

The present invention relates to a pull-on disposable wearing article.

Japanese Unexamined Patent Application Publication No. 1993-317356 (REFERENCE) discloses a pull-on/closed type diaper comprises a pair of fastening strips bonded to transversely opposite side edges of front and rear waist regions so as to extend outward and tear-apart lines provided immediately inside the bonded region in each of the fastening strips along which the front and rear waist regions are disconnected from each other. A distal end of the fastening strip is provided with an engaging region defined by a pressure-sensitive adhesive coated on this distal end or defined by a tape strip provided with a plurality of hooks bonded thereto. This disposable diaper provided with the tear-apart lines and the fastening strips allows the diaper to be used as an open-type diaper after the front and rear waist regions have been disconnected from each other along the tear-apart lines.

While the fastening strips are not actually used before the front and rear waist regions are disconnected from each other along the respective tear-apart lines, there is anxiety that the engaging region might be mischievously contaminated to unworkable condition and/or might come in contact with the wearer's skin and might uncomfortably irritate the wearer's skin.

SUMMARY OF THE INVENTION

It is an object of the present invention to provide a disposable wearing article provided with a fastening means adapted to achieve reconnection of the front and rear waist regions after these waist regions have been disconnected from each other wherein these fastening means can be prevented from being contaminated prior to actual use of the diaper and prevented from coming in contact with the wearer's skin during actual use of the diaper.

According to the present invention, there is provided a pull-on disposable wearing article having a longitudinal direction and a transverse direction, the article comprising: an inner surface, an outer surface, a first panel and a second panel wherein said first and second panels are connected with each other along respective side edges of a waist region as viewed in the transverse direction; at least one of the side edges of the waist region being provided with a tear-apart zone in which the first panel and the second panel can be disconnected from each other; the first panel being provided on the side of inner surface of the first panel in a vicinity of the tear-apart zone with a fastening member adapted to reconnect the cut apart first and second panels to each other; the first panel being provided on the side of the inner surface of the first panel with a cover member adapted to cover the tear-apart zone and the fastening member; and the cover member being peeled off so as to expose the fastening member as the first panel and the second panel are disconnected from each other.

The fastening member provided on the side of the inner surface of the article and covered with the cover member in the manner as has been described above is effective to prevent the fastening member from being mischievously contaminated to the unworkable condition and to prevent the fastening member from coming in contact with the wearer's skin and uncomfortably irritating the wearer's skin. The cover member covering the tear-apart zone and the fastening member ensures that a force exerted on the tear-apart zone to tear the first panel and the second panel apart from each other is transmitted also to the covering member and consequentially the cover member is peeled off so as to expose the fastening member which has been concealed behind the cover member. Reconnection of the first and second panels by the fastening member exposed in this manner allows this wearing article to be used as the open-type article.

While it is not essential which of these first and second panels should be the front panel or the rear panel, the first panel provided with the fastening members is preferably defined as the rear panel. If so, when this wearing article is used as the open-type article, the article can be conveniently put on the wearer lying face up by placing the first panel as the rear panel upon the outer surface of the second panel as the front panel and then by reconnecting these panels to each other.

The first panel and the second panel may be directly or indirectly connected with each other along transversely both side edges of these panels opposed to each other. Direct connection of the first and second panels refers to a state in which the first and second panels are bonded together along the side edges thereof by an adhesive or welding technique. Indirect connection of the first and second panels refers to a state in which members prepared separately from the members constituting the article body are interposed between the first and second panels which are, in turn, respectively bonded to these separate members by an adhesive or a welding technique. Such members adapted to connect the first and second panels will be referred to hereinafter as connector pieces. These connector pieces may be bonded to any one of the inner surface and the outer surface or to both the inner surface and the outer surface of the article.

While the tear-apart zone may be provided along at least one of the side edges of the waist region in a vicinity of which the first and second panels are connected together, it is preferred to provide both side edges of the waist region with the tear-apart zones, respectively, for the purpose of facilitating the article to be put on and taken off from the wearer's body.

"The side edges of the waist region" as used herein should be understood to include, in addition to the borders between the first and second panels, a vicinity thereof.

While it is not essential that the tear-apart zones extend in conformity with the respective borders so far as these tear-apart zones extend along the side edges of the waist region, these tear-apart zones preferably extend in conformity with the respective borders between the first and second panels in order to ensure that the first and second panels can be smoothly disconnected from each other. For example, it is assumed that the first and second panels are directly connected to each other and the borders between these two panels are defined by the respective tear-apart zones. In this case, a strength with which these two panels are bonded together may be appropriately controlled to facilitate these two panels to be disconnected from each other. It is assumed, on the other hand, that these two panels are indirectly connected together by the intermediary of the connector pieces and the tear-apart zones are provided by these connector pieces which, in turn, define the borders between these two panels. In this case, the connector pieces may be made of material which can be torn or broken more easily than the remaining region of the article. Selection of the stock material for the connector pieces in this manner ensures that the first and second panels can be smoothly disconnected from each other. The tear-apart zones are not specified with respect to material as well as configuration thereof so far as the tear-apart zones can be torn or broken more easily than the remaining region of the article. For example, each of the tear-apart zones may be defined by a single slit or a plurality of slits arranged rectilinearly and intermittently in the longitudinal direction of the article to form a so-called perforated line or defined by a cut provided on one of the longitudinally opposite ends of the article as a starting point for tearing apart. In the case of the article including the connector pieces as have been described above, it is possible without departing from the spirit as well as the scope of the invention to form these connector pieces by a sheet material which can be torn or broken more easily than the remaining region of the article so that these connector pieces may define the tear-apart zones. So far as the connector pieces define the tear-apart zones in which the first and second panels are to be disconnected from each other, there is no anxiety even when the article includes the core that the content of the core such as fluff pulp and super-absorbent polymer particles might fall off from the core as the first and second panels are disconnected from each other.

In the case of the embodiment wherein the cover member adapted to cover the fastening member is provided on the side of the inner surface of the first panel and the fastening member is sandwiched between the inner surface of the article and the cover member, the cover member may be releasably bonded over its portion placed upon the tear-apart zone and the fastening member to these tear-apart zone and fastening member by suitable means such as the pressure-sensitive adhesive or the mechanical fastener. However, it is preferred to leave the cover member over its portion placed upon the tear-apart zone and the fastening member free from the tear-apart zone and the fastening member in order to ensure that the cover member can be smoothly peeled off as the first and second panels are disconnected from each other. In this case, it is preferred that the cover member is bonded to the inner surface of the first panel along transversely opposite side edges thereof so as to be securely attached to the inner surface of the first panel.

Preferably, the cover member is formed from a sheet material which can be easily torn in the longitudinal direction or the cover member is provided with a zone which can be easily torn in the longitudinal direction so that the cover member can be more easily peeled off as the first and second panels are disconnected from each other. In the case of the embodiment wherein the cover member is provided with the zone which can be easily torn in the longitudinal direction, such zone is preferably provided adjacent one of transversely opposite side edges of the fastening member opposed to the other side edge in a vicinity of which the tear-apart zone is laid. Such unique positioning of the zone to be easily torn allows the fastening member to be exposed over its substantially entire area as the cover member is torn in the zone adapted to be easily torn. Therefore, no operation is required to peel the cover member and thereby to expose the fastening member in addition to the operation of disconnecting the first and second panels from each other. This unique positioning advantageously results in efficiently utilizing the fastening area provided by the fastening member. The zone adapted to be easily torn may be defined by providing the cover member with a single slit or a plurality of slits extending in the longitudinal direction. Preferably, the cover member is provided with a plurality of slits. More preferably, the cover member is provided with a plurality of slits defining so-called perforated line extending from the upper end to the lower end of the cover member.

The term "cut off", "tear apart" or "break" as used herein refers to an operation which can be achieved with bare hands.

In the disposable wearing article according to the present invention, the fastening member is prevented from being contaminated prior to actual use thereof and prevented from coming in contact with the wearer's skin during actual use thereof. This is because the fastening member is provided on the side of the inner surface of the chassis and the fastening member is covered over the entire surface thereof with the cover member.

The other constructions as well as the other materials according to the present invention should be understood in reference with description of the preferred embodiment. However, the preferred embodiment as will be described later should not be considered to limit the present invention.

DETAILED DESCRIPTION OF THE PREFERRED EMBODIMENTS

Details of a disposable wearing article according to the present invention will be more fully understood from the description of the disposable diaper given hereunder as an embodiment with reference to the accompanying drawings.

Figure 1:
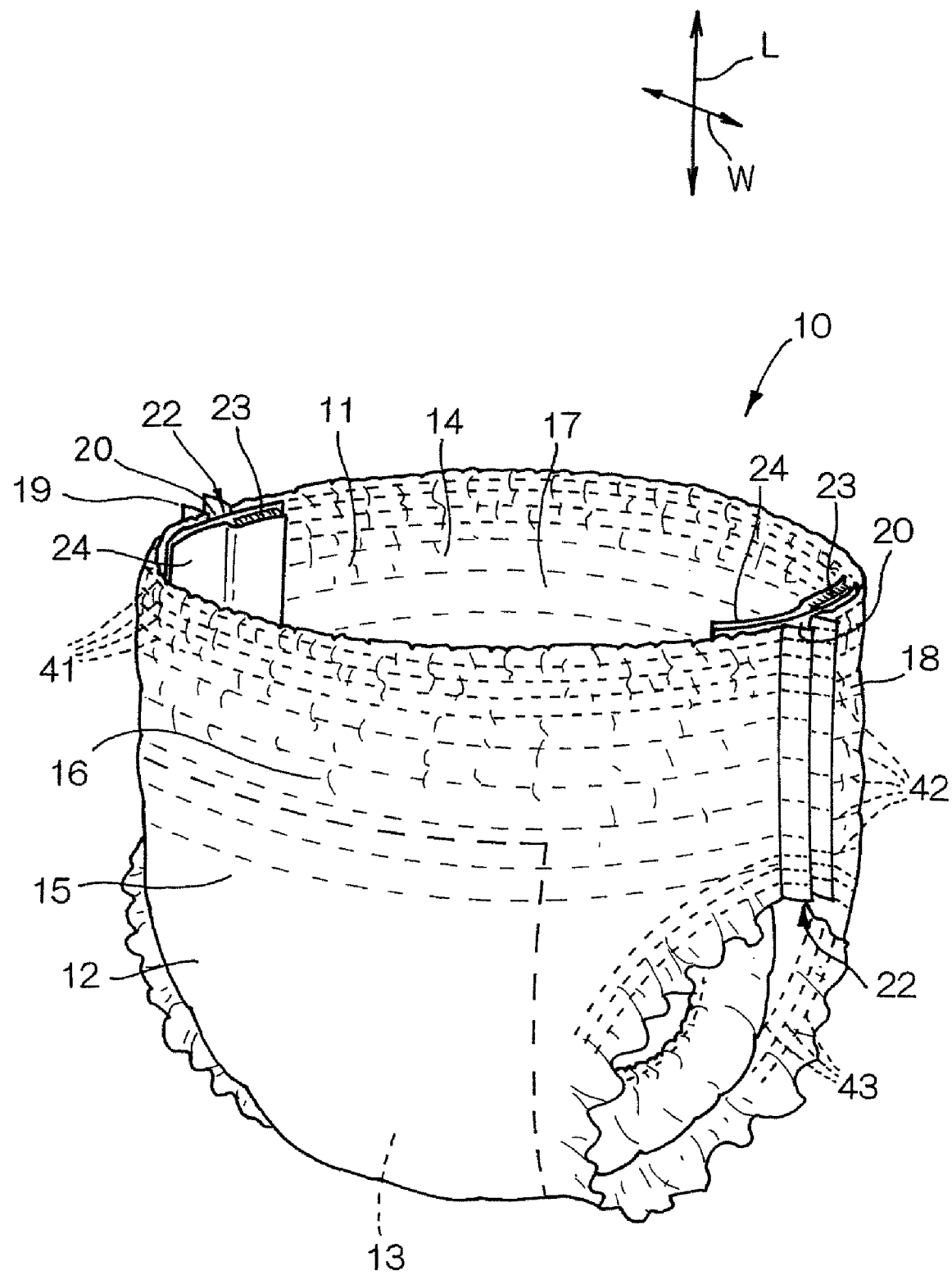
FIG. 1 is a perspective view showing a pull-on/closed type disposable diaper as an embodiment of the present invention.
Figure 2:
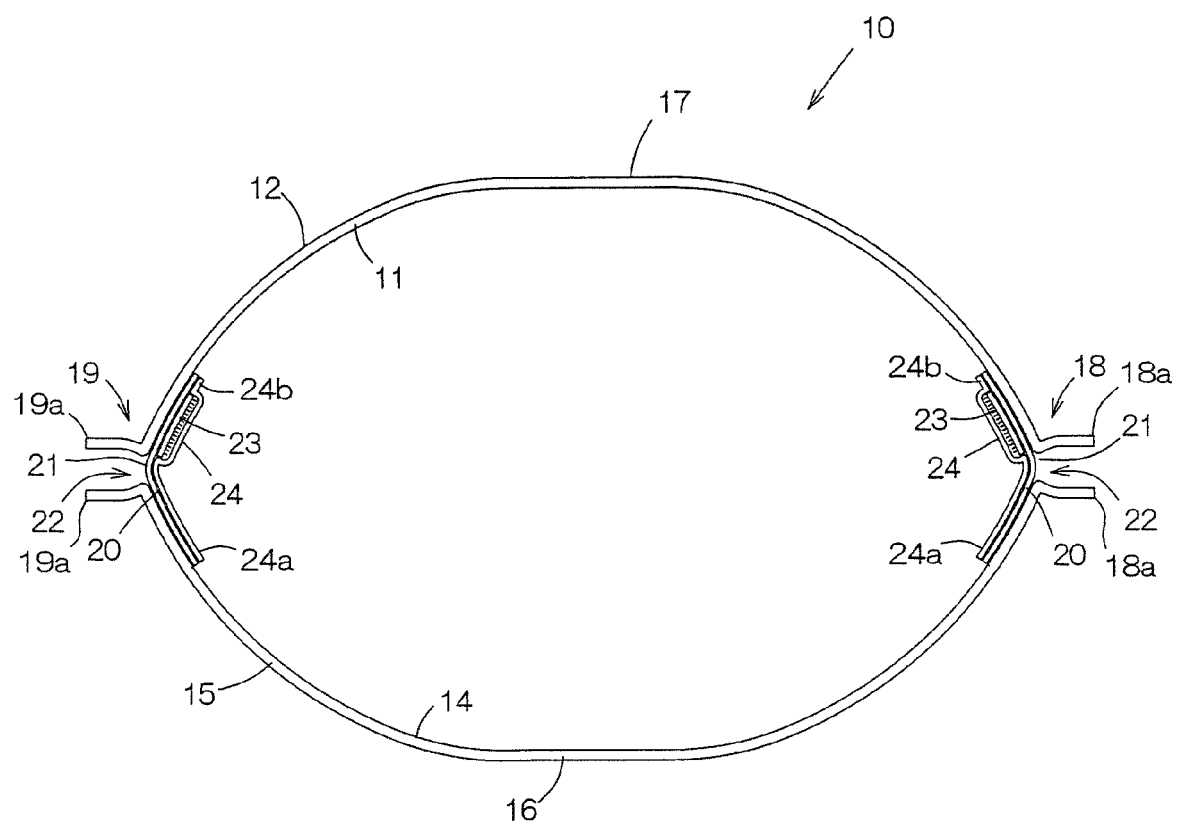
FIG. 2 is an end elevational view showing the disposable diaper of FIG. 1 as viewed from just above a waist-hole thereof.
Figure 3:
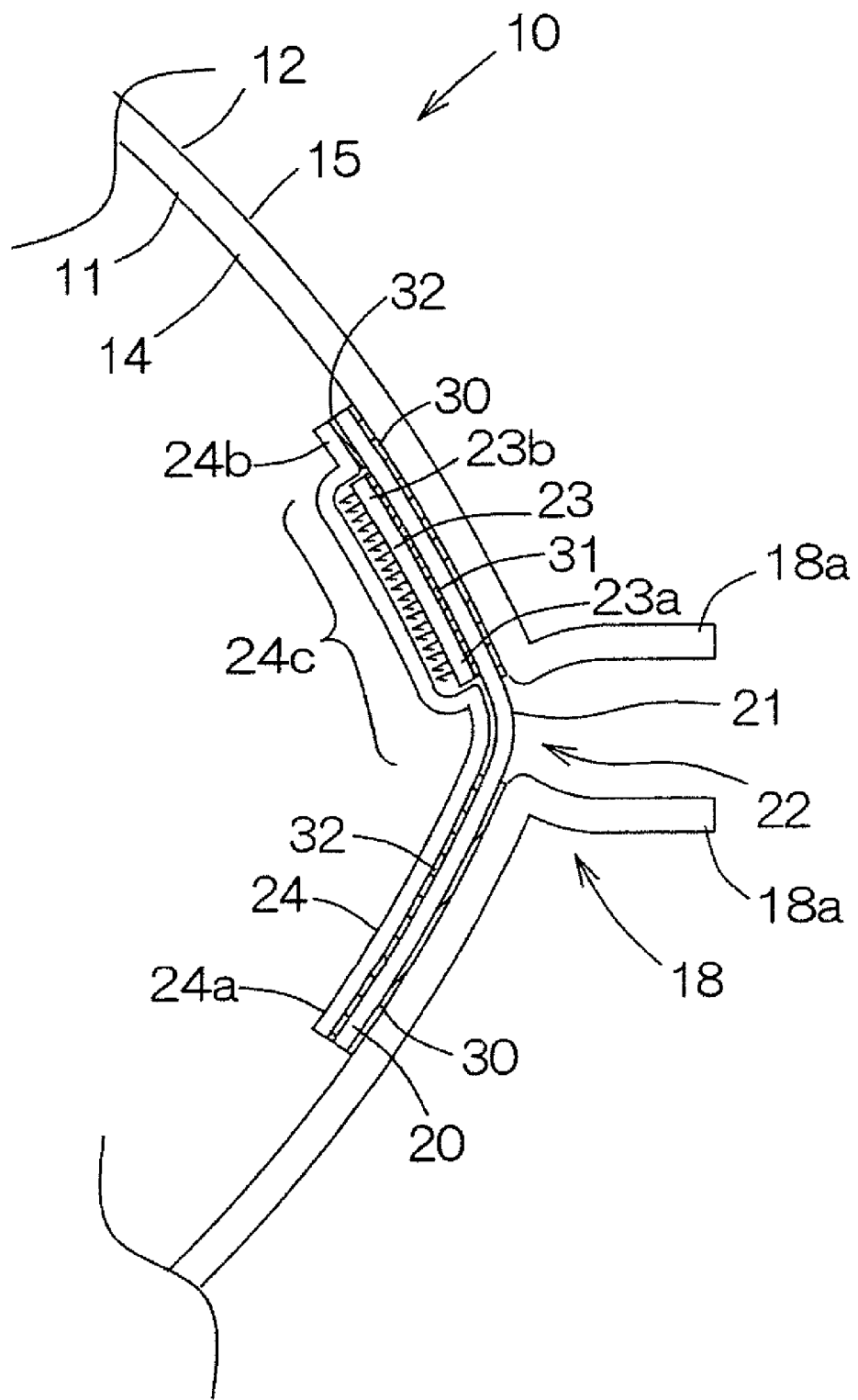
FIG. 3 is a scale-enlarged showing one of side edges of the disposable diaper's waist region.

FIG. 1 is a perspective view showing a pull-on/closed type disposable diaper, FIG. 2 is an end elevational view showing the disposable diaper of FIG. 1 as viewed from directly above a waist-hole and FIG. 3 a scale-enlarged showing one of opposite side edges of diaper's waist region.

A disposable diaper 10 comprises a liquid-pervious topsheet 11, a liquid-impervious backsheet 12 and a body fluid absorbent core 13 sandwiched between these two sheets 11, 12. The disposable diaper 10 has a longitudinal direction L, a transverse direction W, an inner surface 14, an outer surface 15, and a front panel 16 and a rear panel 17 opposed to each other so as to form the waist region. As shown, the front panel 16 and the rear panel 17 are indirectly connected to each other along side edges 18, 19 of these panels 16, 17 opposed one to another by a pair of connector pieces 20, whereupon a waist-hole and a pair of leg-holes are formed. The connector piece 20 is bonded to the inner surface 14 by an adhesive 30 so as to cross over both the front panel 16 and the rear panel 17 (See FIGS. 2 and 3).

The disposable diaper 10 is provided along the side edges 18, 19 of the waist region with a pair of tear-apart zones 22, respectively, in which the front panel 16 and the rear panel 17 can be disconnected from each other. More specifically, between a pair of ears 18a, 18a and between a pair of ears 19a, 19a extending outward from the side edges 18, 19 of the waist region, respectively, the tear-apart zones 22 define, on the connector pieces 20, borders 21 between the front panel 16 and the rear panel 17 (See FIG. 2). While the desired effect of the tear-apart zone 22 may be obtained so far as it is provided along any one of the side edges 18, 19, it is preferred to provide the both side edges 18, 19 with the tear-apart zones 22, as shown. This is because the front panel 16 and the rear panel 17 may be disconnected from each other along the tear-apart zones 22 with the bare hands to develop the disposable diaper 10 completely and thereby to facilitate the disposable diaper 10 to be put on and taken off from the wearer's body.

The waist-hole and the leg-holes are respectively provided with waist elastic members 41 and leg elastic members 43 in the well known manner. Below the waist elastic members 41, each of the front and rear panels 16, 17 is provided with auxiliary waist elastic members 42 extending in the transverse direction and having a tensile stress lower that that of the waist elastic members 41 as well as that of the leg elastic members 43. These waist elastic member 41, auxiliary waist elastic members 42 and leg elastic members 43 are sandwiched between the topsheet 11 and the backsheet 12 and bonded in a stretched state to at least one of the top- and backsheets 11, 12 by adhesives (not shown).

Both the waist elastic members 41 and the auxiliary waist elastic members 42 are divided into respective front halves laid on the front panel 16 and respective rear halves laid on the rear panel 17. These front and rear halves are not contiguous one to another at the side edges 18, 19 of the waist region. In other words, neither the waist elastic members 41 nor the auxiliary waist elastic members 42 are present on the borders 21 between the front and rear panels 16, 17 defined by the tear-apart zones 22.

The leg elastic members 43 extend along an upper half of each leg-hole periphery. Like the waist elastic members 41, the leg elastic members 43 also is divided into a font half laid on the front panel 16 and a rear half laid on the rear panel 17. These front and rear halves are not contiguous to each other at the side edges 18, 19 of the waist region. In other words, the leg elastic members 43 is not present on the borders 21 between the front and rear panels 16, 17 defined by the tear-apart zones 22.

Such feature that the tear-apart zones 22 are devoid of these elastic members 41, 42, 43 facilitates the front and rear panels 16, 17 to be disconnected from each other in these tear-apart zones 22 without botheration due to these elastic members 41, 42, 43 which might bonk the hands as these elastic members are cut off, if these elastic members laid on the front panel 16 are contiguous to these elastic members laid on the rear panel 17.

A pair of fastening members 23 is provided on the inner surface 14 of the rear panel 17 in the vicinity of the tear-apart zones 22 at the side edges 18, 19 of the waist region. These fastening members 23 are adapted to reconnect the front and rear panels 16, 17 having been once disconnected from each other and have a stiffness higher than a stiffness of the connector pieces 20. As shown in FIGS. 2 and 3, the fastening members 23 are provided preferably so as to extend along the respective side edges of the rear panel 17. The fastening members 23 provided in this manner allow the connector pieces 20 to be torn apart along the side edges of the respective fastening members 23 and thereby facilitate the front and rear panels 16, 17 to be disconnected from each other.

The fastening members 23 are bonded to the respective connector pieces 20 by an adhesive 31. While the entire surface of the fastening member 23 to be bonded to the associated connector piece 20 is coated with the adhesive 31 in the case of the illustrated disposable diaper 10, the surface of the fastening member 23 to be bonded to the associated connector piece 20 may be partially coated with the adhesive 31 so far as a bonding strength sufficient for practical use of the disposable diaper 10 can be obtained. However, when the surface of the fastening member 23 to be bonded to the associated connector piece 20 is partially coated with the adhesive 31, it will be preferred for the reason as will be described below to coat opposite side edges 23a, 23b or at least the side edge 23b of the fastening member 23 as viewed in the transverse direction W with the adhesive 31. Now it is assumed that the front and rear panels 16, 17 are disconnected from each other and then reconnected with each other by the fastening members 23 in order to use the disposable diaper 10 as the open-type diaper. If the fastening members 23 are bonded to the inner surface 14 of the rear panel 17 along the side edges 23a thereof located aside toward the front panel 16 by the adhesive 31, it is likely that the front and rear panels 16, 17 might be readily separated from each other under a shearing force exerted upon the fastening members 23. On the contrary, if the fastening members 23 are bonded to the inner surface 14 of the rear panel 17 along the side edges 23b thereof by the adhesive 31, the front and rear panels 16, 17 are not so readily separated from each other as in the case described above that the front and rear panels 16, 17 might be separated from each other even when the area over which the adhesive 31 is coated is the same as in the former case.

While hook members constituting a so-called mechanical fastener are used as the fastening members 23 in the illustrated embodiment, it is possible without departing from the scope as well as the spirit of the invention to use tape strips coated with a pressure-sensitive adhesive as the fastening members 23. Preferably, in this case, sheet strips having release characteristics are used as cover members 24 or sheet strips are provided with appropriate releasability, for example, by coating the surfaces of the sheet strips destined to face the respective fastening members 23 with release agent so that the sheet strips may be easily peeled off from the respective fastening members 23.

The fastening members 23 are thus covered with the respective cover members 24. These cover members 24 are provided on the side of the inner surface 14 so as to cross over both the front panel 16 and the rear panel 17 and to cover the respective fastening members 23 as well as the respective tear-apart zones 22 (See FIG. 3). Each of these cover members 24 has lateral segments 24a, 24b as viewed in the transverse direction W bonded to the connector piece 20 by an adhesive 32 and a segment 24c placed upon but bonded neither to the tear-apart zone 22 nor to the fastening member 23. Such a unique arrangement that the cover member 24 is left free from the tear-apart zone 22 as well as from the fastening member 23 facilitates the front and rear panels 16, 17 to be disconnected from each other with the bare hands. This is because the tearing force exerted on the tear-apart zone 22 is smoothly transmitted to the remaining part of the cover member 24 and no force is required to peel the cover member 24 off from the surface of the fastening member 23. The construction consisting of the connector piece 20, the fastening member 23 and the cover member 24 placed upon and bonded to one another as illustrated is advantageous in that these connector piece 20, fastening member 23 and cover member 24 can be prepared as a unit adapted to be collectively incorporated into the disposable diaper 1.

Figure 4:
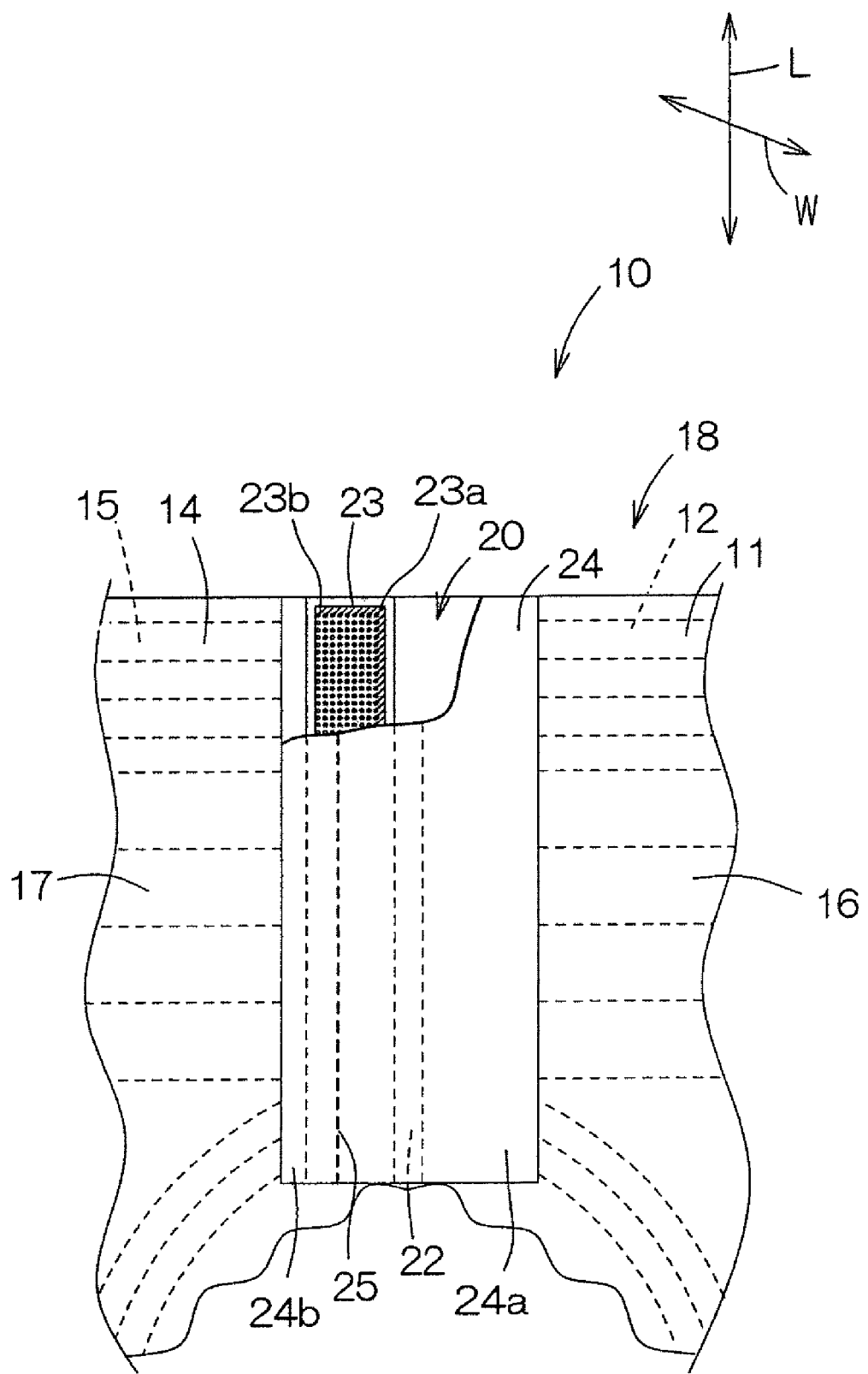
FIG. 4 is a scale-enlarged partial view showing the side edge of the waist region as viewed from the side of the inner surface of the disposable diaper.
Figure 5:
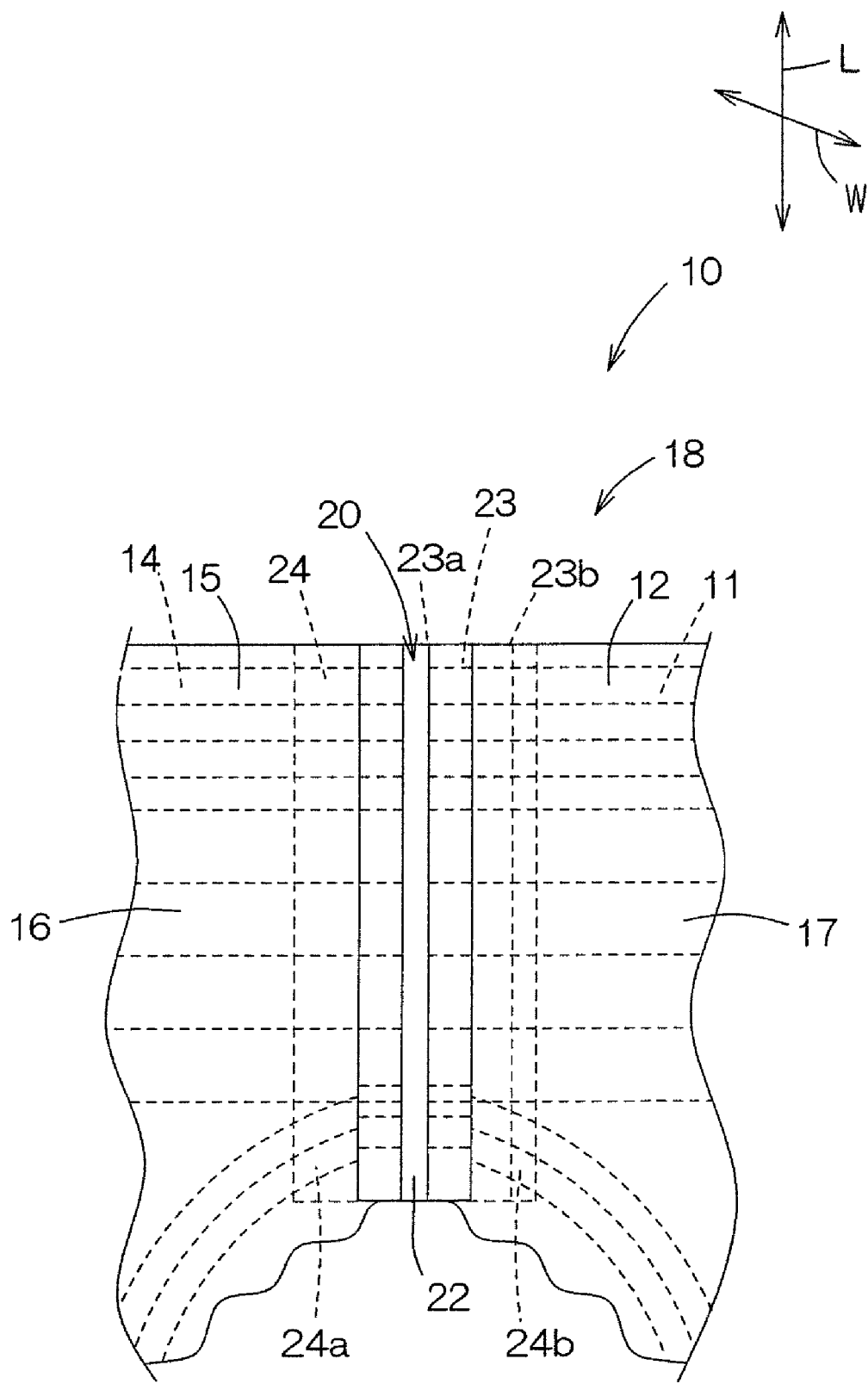
FIG. 5 is a scale-enlarged view showing the side edge of the waist region as viewed from the side of the outer surface of the disposable diaper.
Figure 6:
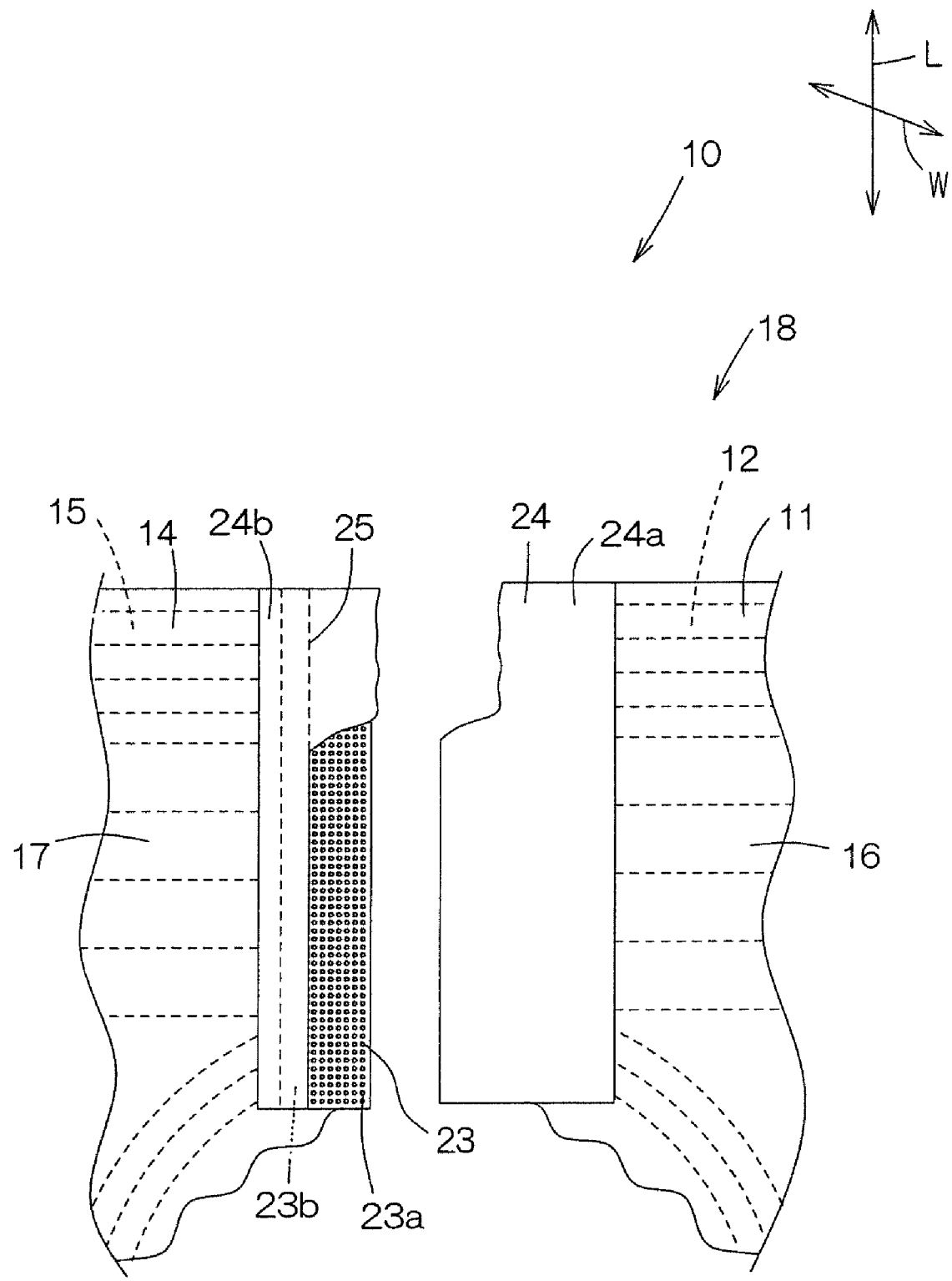
FIG. 6 is a view similar to FIG. 4, showing the side edge of the waist region after the front and rear panels have been disconnected from each other.

FIG. 4 is a scale-enlarged view showing the side edge 18 of the waist region as viewed from the side of the inner surface 14 of the disposable diaper 10, FIG. 5 is a scale-enlarged view showing the side edge 18 of the waist region as viewed from the side of the outer surface 15 of the disposable diaper 10 and FIG. 6 is a view similar to FIG. 4, showing the side edge 18 of the waist region after the front panel 16 and the rear panel 17 have been disconnected from each other along the tear-apart zone 22.

As shown in FIG. 4, the cover member 24 covering the tear-apart zone 22 and the fastening member 23 along the side edge 18 of the waist region is provided with a line 25 along which the cover member 24 is readily cut off in the longitudinal direction L. Such easily torn line 25 is preferably realized by a single slit or a plurality of slits arranged intermittently in the longitudinal direction L and more preferably realized by a perforated line extending from the upper end to the lower end of the cover member 24 as shown in FIG. 4. While this easily torn line 25 shown in FIG. 4 is provided on the fastening member 23 in the vicinity of the side edge 23b opposite to the side edge 23a of the fastening member 23 as viewed in the transverse direction W wherein the tear-apart zone 22 lies in the vicinity of the side edge 23a, it is possible without departing from the spirit as well as the scope of the invention to provide the line 25 along the edge of the fastening member 23 or outside the edge of the fastening member 23 in the vicinity of the side edge 23b (not shown). By providing the line 25 adapted to be easily torn outside the edge of the fastening member 23, it is ensured that the fastening member 24 is exposed over its entire length in the transverse direction W as the cover member 24 is cut off along the line 25 adapted to be easily torn and peeled off from the fastening member 23. Consequently, the fastening surface of the fastening member 23 can be effectively utilized.

To tear the front and rear panels 16, 17 apart from each other, both sides of the respective tear-apart zones 22 as viewed in the transverse direction W are held with both hands at the side edges 18 and/or the side edges 19 of the waist region and then appropriate tearing force is exerted on the respective connector pieces 20 in the longitudinal direction L. Such tearing force is transmitted also to the cover members 24 placed upon the respective connector pieces 20 on the side of the inner surface 14. The cover members 24 are torn apart first together with the associated connector pieces 20 in the tear-apart zones 22 and then torn apart along the respective easily torn lines 25 (See FIG. 6). Along the easily torn lines 25, the cover members 24 can be torn by a force lower than that required to tear the cover members 24 in the remaining zone and therefore the front and rear panels 16, 17 can be easily disconnected from each other even though the tear-apart zones 22 are covered with the cover members 24.

With the disposable diaper 10 constructed in the manner as has been described above, the cover members 24 are peeled off so as to expose the fastening members 23 just as the front and rear panels 16, 17 are disconnected from each other.

The present invention may be exploited also in a manner that the front and rear panels 16, 17 may be directly connected to each other, i.e., using none of the connector pieces 20. In this case, the front and rear panels 16, 17 is directly bonded to each other by well known art so that a bonding strength may be controlled at a degree allowing the front and rear panels 16, 17 to be easily disconnected from each other with the hands. In this case, the fastening members 20 and the cover members 24 are directly bonded to the rear panel 17 (or the front panel 16). Even when the front and rear panels 16, 17 are directly connected to each other in this manner, the cover members 24 are peeled off to expose the fastening members 23 so far as the disposable diaper 10 is provided with the fastening members 20 and the cover members 24 constructed as has been described above.

A stock material for the topsheet 11 may be selected from the group consisting of a nonwoven fabric made of thermoplastic synthetic resin fibers having a basis weight in a range of 10 to 30 g/m$^2$ and a monoaxially or biaxially oriented porous film of thermoplastic synthetic resin having a thickness in a range of 10 to 30 μm.

A stock material for the backsheet 12 may be selected from the group, for example, consisting of a biaxially oriented film of thermoplastic synthetic resin having a thickness in a range of 20 to 50 μm and a composite sheet comprising such film and nonwoven fabric of thermoplastic synthetic resin fibers having a basis weight in a range of 20 to 50 g/m$^2$ intermittently bonded to each other. Provided that the hook member constituting a so-called mechanical fastener is used as the fastening member 23, the backsheet 12 should have a piled surface adapted to be engaged with the hook member.

The core 13 may comprise, for example, a mixture of fluff pulp and super-absorbent polymer particles wrapped with a sheet material such as a tissue paper or nonwoven fabric which is outstanding in its liquid-permeability or both its liquid-permeability and liquid-diffusibility or fluff pulp alone wrapped with such sheet material.

A stock material for the connector pieced 20 may be selected from the group, for example, consisting of a nonwoven fabric made of thermoplastic synthetic resin fibers such as polyethylene, polypropylene or polyester, a film made of such synthetic resin, and a laminate of these nonwoven fabric and film. Examples of the nonwoven fabric include a spun bond nonwoven fabric made of polyethylene fibers having a fineness in a range of 1 to 5 dtx and a basis weight in a range of 20 to 50 g/m$^2$ and an SMS nonwoven fabric which comprises a laminate of a spun bond nonwoven fabric made of polyethylene fibers having a fineness in a range of 1 to 5 dtx and a basis weight of 6.5 g/m$^2$, a melt blown nonwoven fabric made of polyethylene fibers having a fineness in a range of 0.2 to 1 dtx and a basis weight of 2 g/m$^2$ and a spun bond nonwoven fabric made of polyethylene fibers having a fineness in a range of 1 to 5 dtx and a basis weight of 6.5 g/m$^2$. Examples of the film include a monoaxially or biaxially oriented polyethylene film and a polypropylene film having a thickness in a range of 20 to 50 μm. The nonwoven fabric having its component fibers notably oriented in a specific direction or the film having its polymer chain notably oriented in a specific direction may be used with such specific direction conformed to the longitudinal direction of the disposable diaper 10 in order to facilitate the connector pieces 20 to be torn in the longitudinal direction. A so-called perforated line also facilitates the connector piece 20 to be easily torn.

When the hook member constituting a so-called mechanical fastener is used as the fastening member 23, the hook of well known art may be used. When the tape strip coated with a pressure-sensitive adhesive is used as the fastening member 23, the tape strip formed by the plastic film of well known art may be coated with the pressure-sensitive adhesive of well known art.

A stock material for the cover member 24 may be selected from the group, for example, consisting of a nonwoven fabric made of thermoplastic synthetic resin fibers such as a polyethylene, polypropylene or polyester which may be used as a stock material for the connector piece 20, a film made of such synthetic resin and a laminate of these nonwoven fabric and film.

Bonding of the connector piece 20, the fastening member 23 and the cover member 24 may be carried out by adhesion using a hot melt adhesive or the like or a welding technique such as thermal or ultrasonic welding technique so far as a bonding strength appropriate for practical use of the disposable diaper 10 can be obtained. Such bonding may be continuous or intermittent.

A stock material for the elastic members 41, 42, 43 may be selected from the group, for example, consisting of a rubber yarn and flat rubber belt made of well known material such as a natural rubber, synthetic rubber or urethane foam.

The present invention is applicable for, in addition to the pull-on/closed type disposable diaper, pull-on/closed type disposable wearing article such as training pants, pants for incontinent patient or sanitary shorts.

The entire discloses of Japanese Patent Application No. 2005-129994 filed on Apr. 27, 2005 including specification, drawings and abstract are herein incorporated by reference in its entirety.

What is claimed is:

1. A pull-on disposable wearing article having a longitudinal direction and a transverse direction, said article comprising:
   a first panel and a second panel wherein said first and second panels are connected with each other along respective side edges of a waist region of said article as viewed in the transverse direction;
   at least one of said side edges of the waist region being provided with a tear-apart zone in which said first panel and said second panel can be disconnected from each other by material failure in said tear-apart zone;
   a fastening member provided on the side of an inner surface of said first panel in a vicinity of said tear-apart zone, and adapted to reconnect said first and second panels to each other after said first and second panels have been disconnected from each other by material failure in said tear-apart zone;
   a cover member provided on the side of the inner surface of said first panel, and covering said tear-apart zone and said fastening member; and
   said cover member being peeled off so as to expose said fastening member as said first panel and said second panel are disconnected from each other by material failure in said tear-apart zone;
   wherein said cover member comprises a tear line along which said cover member is manually tearable, and said tear line laid adjacent one of transversely opposite side edge of said fastening member, and said tear-apart zone is laid in a vicinity of the other side edges of said fastening member.

2. The wearing article as defined by claim 1, wherein said cover member is bonded along transversely opposite side edges thereof to first panel and the second panel, respectively, and is free of direct attachment to both said tear-apart zone and said fastening member.

3. The wearing article as defined by claim 1, wherein said tear line is defined by a single slit or a plurality of slits arranged in said longitudinal direction.

4. The wearing article as defined by claim 1, wherein said tear-apart zone defines a border between said first panel and said second panel.

5. The wearing article as defined by claim 1, wherein said first panel and said second panel are indirectly connected to each other along at least one of the side edges of the waist region a connector piece comprising said tear-apart zone.

6. The wearing article as defined by claim 5, wherein said fastening member has a stiffness higher than said connector piece to facilitate tearing of said connector piece in the tear-apart zone along one of transversely opposite side edges of said fastening member.

7. The wearing article as defined by claim 5, wherein said connector piece comprises one selected from the group consisting of
   (a) a non-woven fabric having component fibers oriented in the longitudinal direction for facilitating tearing of said connector piece in the longitudinal direction, and
   (b) a plastic film having polymer chains oriented in the longitudinal direction for facilitating tearing of said connector piece in the longitudinal direction.

8. The wearing article as defined by claim 5, wherein said connector piece comprises
   opposite first and second end portions bonded directly to said first and second panels, respectively, and
   a middle portion connecting said first and second end portions, bridging a gap between the first and second panels, and free of direct bonding to any of said first and second panels, said middle portion defining said tear-apart zone;
   wherein said fastening member is bonded directly to said first end portion of said connector piece so that said first end portion of said connector piece is sandwiched between said fastening member and said first panel.

9. The wearing article as defined by claim 8, wherein said fastening member has transversely opposite first and second side edges, and the second side edge of said fastening member is closer to said middle portion of said connector piece than the first side edge of said fastening member to facilitate tearing of said connector piece in the tear-apart zone extending along said second side edge of said fastening member.

10. The wearing article as defined by claim 9, wherein said cover member comprises:
    opposite first and second end sections bonded directly to the first and second end portions of the connector piece, respectively, and
    a middle section covering and free of direct attachment to both the fastening member and the middle portion of the connector piece, the fastening member being sandwiched between the middle section of the cover member and the first end portion of the connector piece.

11. The wearing article as defined by claim 10, whereby the fastening member is exposed when the cover member and the connector piece are torn along the first and second side edges of the fastening member, respectively.

12. The wearing article as defined by claim 11, wherein strengths of the connector piece in the tear-apart zone and of the cover member along the tear line are lower than bonding strengths between the cover member and the connector piece and between the connector piece and the first and second panels.

13. The wearing article as defined by claim 11, wherein said first and second panels comprise free edges adjacent and free of direct bonding to the connector piece, and wherein said free edges define gripping portions where the first and second panels are grippable by hand for facilitating manual tearing of said connector piece and said cover member.

14. The wearing article as defined by claim 11, wherein a strength of the connector piece in the tear-apart zone is higher than that of the cover member along the tear line.

15. The wearing article as defined by claim 1, wherein said first and second panels are bonded directly to one another by one selected from the group consisting of (i) adhesive spots and (ii) welding sites; and
    a bonding strength at said spots or sites is sufficiently low for allowing manual separation of said first and second panels at said sites which define the tear-apart zone.

16. The wearing article as defined by claim 15, wherein said cover member comprises:
    opposite first and second end sections bonded to the first and second panels, respectively, and
    a middle section covering and free of direct attachment to both the fastening member and the tear-apart zone, the fastening member being sandwiched between the middle section of the cover member and the first panel.

17. The wearing article as defined by claim 16, wherein
said fastening member has transversely opposite first and second side edges,
the second side edge of said fastening member is closer to said tear-apart zone than the first side edge of said fastening member, and
said cover member further comprises a tear line located adjacent and along the first side edge of said fastening member, whereby the fastening member is exposed when the cover member and the tear-apart zone are torn along the first and second side edges of the fastening member, respectively.

18. The wearing article as defined by claim 1, consisting of only one said tear-apart zone which is disposed along one of the side edges of the waist region.

19. The wearing article as defined by claim 1, wherein said cover member is bonded along transversely opposite side edges thereof to the first panel and the second panel, respectively, and is releasably bonded by pressure-sensitive adhesive to at least one said tear-apart zone and said fastening member.

* * * * *